US011972849B2

(12) United States Patent
Isom (10) Patent No.: US 11,972,849 B2
(45) Date of Patent: Apr. 30, 2024

(54) SYSTEMS AND METHODS FOR PROVIDING IMPROVED DATABASE FUNCTIONALITY

(71) Applicant: Michael Isom, West Valley, UT (US)

(72) Inventor: Michael Isom, West Valley, UT (US)

(73) Assignee: Michael Isom, Salt Lake City, UT (US)

(*) Notice: Subject to any disclaimer, the term of this patent is extended or adjusted under 35 U.S.C. 154(b) by 0 days.

(21) Appl. No.: 17/747,622

(22) Filed: May 18, 2022

(65) Prior Publication Data

US 2022/0375561 A1 Nov. 24, 2022

Related U.S. Application Data

(60) Provisional application No. 63/226,966, filed on Jul. 29, 2021, provisional application No. 63/190,424, filed on May 19, 2021.

(51) Int. Cl.
*G16H 15/00* (2018.01)
*G06N 3/02* (2006.01)
*G16H 10/60* (2018.01)

(52) U.S. Cl.
CPC ............. *G16H 15/00* (2018.01); *G06N 3/02* (2013.01); *G16H 10/60* (2018.01)

(58) Field of Classification Search
CPC ........... G16H 15/00; G16H 10/60; G06N 3/02
See application file for complete search history.

(56) References Cited

U.S. PATENT DOCUMENTS

2007/0241861 A1* 10/2007 Venkatanna ............ G06F 21/40
340/5.52
2017/0159138 A1* 6/2017 Tarcic .................. C12Q 1/6886

* cited by examiner

*Primary Examiner* — Loc Tran
(74) *Attorney, Agent, or Firm* — Greenberg Traurig, LLP (57) ABSTRACT

The present disclosure may include methods, systems, and computer-readable media for optimizing database functionality. For example, one method may include receiving test data from multiple different test data sources for a specified user under test. The method may further include training a machine learning model to: access the test data received from the test data sources for the same user under test, identify which disparate substances or conditions are being tested on the user by each of the different test data sources, and determine a relevance score for each of the identified substances or conditions being tested by the different test data sources. The method may also include generating an illustration of combined test results for the user under test that includes those substances or conditions that meet at least a minimum relevance score. Other systems, methods, and computer-readable media are also described.

18 Claims, 3 Drawing Sheets

SYSTEMS AND METHODS FOR PROVIDING IMPROVED DATABASE FUNCTIONALITY

CROSS-REFERENCE TO RELATED APPLICATIONS

This application claims priority to and the benefit of U.S. Provisional Application No. 63/190,424, entitled "Systems and Methods for Providing Improved Drug Database Functionality," filed on May 19, 2021, and U.S. Provisional Application No. 63/226,966, entitled "Systems and Methods for Providing Improved Drug Database Functionality," filed on Jul. 29, 2021, the entirety of which applications are incorporated by reference herein.

BACKGROUND

Every day, many people across the country are subject to medical tests. These medical tests are used by employers, physicians, judges, government entities, and other people to make decisions regarding the individuals that are subject to the medical tests, as well as public health guidance, fiscal policy, and legislation. Results from these medical tests are typically stored in separate databases that lack communication with each other. As such, a single individual may be subject to a medical test with an employer, may be subject to another medical test from a parole officer, and may be subject to still another medical test from a physician. Each of these medical tests may use different medical panels and may return disparate data. Accordingly, this may lead to confusion among the various entities that use these medical tests to make informed decisions.

BRIEF SUMMARY

Embodiments described herein are directed to systems and apparatuses for optimizing database functionality. In one embodiment, computer-implemented method may include receiving test data from multiple different test data sources for a specified user under test. The test data may represent any type of medical test results including tests for different medical conditions, different types of drugs, chemicals, medications, or other types of substances. The method may further include training a machine learning model to: access the test data received from the test data sources for the same user under test, identify which disparate substances or medical conditions are being tested on the user by each of the different test data sources, and determine a relevance score for each of the identified substances being tested by the different test data sources. The method may also include generating an illustration of combined test results for the user under test that includes those substances or medical conditions that meet at least a minimum relevance score.

In some embodiments, training the machine learning model to identify which disparate substances or conditions are being tested on the user by each of the different test data sources may include determining that at least two of the different test data sources format the test data in different manner.

In some cases, the method may further include altering at least a first data format of the received test data to align with a second determined data format. In some examples, training the machine learning model to identify which disparate substances or conditions are being tested on the user by each of the different test data sources may include determining that at least two of the different test data sources identify substances under test using different identifiers.

In some embodiments, the method may further include training the machine learning model to compare similarities in substance identifiers in the different test data sources to determine if at least two substances having different identifiers are testing for the same substance. In some cases, the method may further include training the machine learning model to compare similarities in detected amounts of substance in the different test data sources to determine if at least two substances having different identifiers are testing for the same substance.

In some examples, the method may further include training the machine learning model to compare both similarities in substance identifiers and similarities in detected amounts of substance in the different test data sources to determine if at least two substances having different identifiers are testing for the same substance.

In some cases, the method may further include authenticating a monitoring user that is authorized to view the illustration of combined test results and presenting the generated illustration of combined test results to the authenticated monitoring user. In some embodiments, training the machine learning model to determine the relevance score for the identified substances may include determining whether the identified substances being tested are indicative of a specified health condition of the user under test. In some examples, training the machine learning model to determine the relevance score for the identified substances may include determining a degree to which the identified substances being tested are indicative of a specified health condition of the user under test.

In some embodiments, a system may be provided. The system may include at least one physical processor and physical memory comprising computer-executable instructions that, when executed by the physical processor, cause the physical processor to: receive test data from different test data sources for a specified user under test, train a machine learning model to: access the test data received from the plurality of test data sources for the same user under test, identify which disparate substances or conditions are being tested on the user by each of the different test data sources, and determine a relevance score for each of the identified substances or conditions being tested by the different test data sources. The physical processor may further generate an illustration of combined test results for the user under test that includes those substances or conditions that meet at least a minimum relevance score.

In some examples, the test data sources may include medical test administration offices. In some cases, the medical test administration offices may implement a specific input format as a precondition for having their corresponding test data included in the generated illustration of combined test results. In some embodiments, the test data may correspond to a medical drug test. In some case, the medical drug test may include a basic metabolic panel, a comprehensive metabolic panel, or a complete blood count.

In some examples, training the machine learning model to determine the relevance score for the identified substances may include determining whether the identified substances being tested are indicative of a specified health condition of the user under test. In some cases, training the machine learning model to determine the relevance score for the identified substances may include determining a degree to which the identified substances being tested are indicative of a specified health condition of the user under test. Still further, in some cases, training the machine learning model to identify which disparate substances are being tested on the user by each of the different test data sources may include determining that at least two of the different test data sources identify substances under test using different identifiers. In some cases, the physical processor may further train the machine learning model to compare both similarities in substance identifiers and similarities in detected amounts of substance in the different test data sources to determine if at least two substances having different identifiers are testing for the same substance.

In some embodiments, a non-transitory computer-readable medium may be provided that includes one or more computer-executable instructions which, when executed by at least one processor of a computing device, cause the computing device to: receive test data from a plurality of different test data sources for a specified user under test, train a machine learning model to: access the test data received from the test data sources for the same user under test, identify which disparate substances or conditions are being tested on the user by each of the different test data sources, and determine a relevance score for each of the identified substances or conditions being tested by the different test data sources, and generate an illustration of combined test results for the user under test that includes those substances or conditions that meet at least a minimum relevance score.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which.

DETAILED DESCRIPTION

As will be described further below, various types of computer systems may be implemented to perform methods for optimizing medical test database functionality. The methods performed for optimizing medical test database functionality may include receiving test data from multiple different medical test administration offices for a specified user that is being tested. The methods may further include training a machine learning model to analyze the test data received from the various test data sources, to identify which disparate substances or medical conditions are being tested by each of the test data sources, and to determine a relevance score for each of the identified substances or medical conditions being tested by the different test data sources. The methods may then include generating an illustration of combined test results for the specified user under test that includes those substances that meet at least a minimum relevance score.

Figure 1:
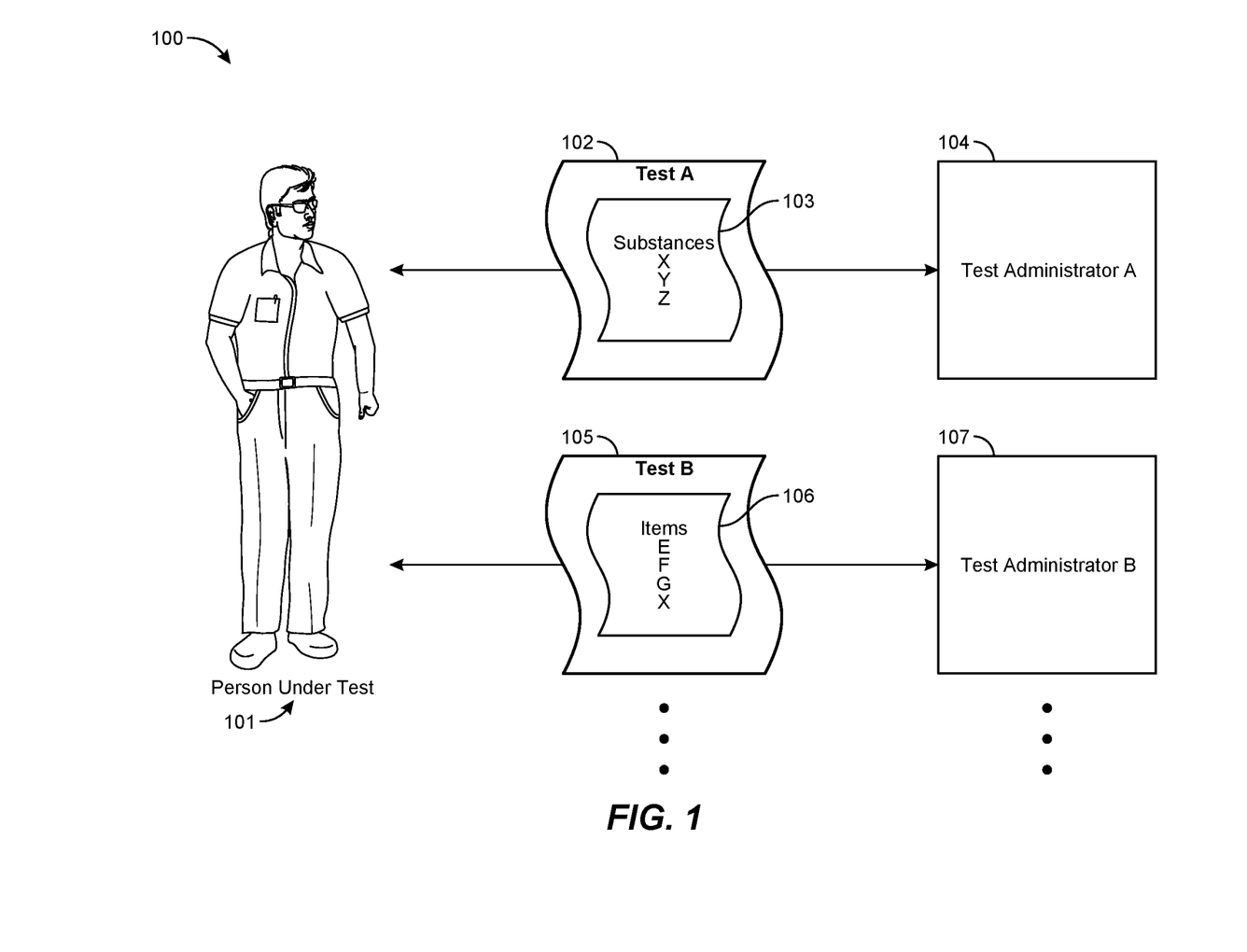
FIG. 1 illustrates an embodiment in which a user under test is subjected to multiple different test administrations.

As noted above, many people undergo medical tests each day. These medical tests may include tests for different drugs, different chemicals, or other conditions or substances. In some cases, these people are subject to different medical tests from different providers. For instance, as shown in FIG. 1, an employer may use test administrator A (104) to perform drug tests, for example, for their employees, a city judge may use test administrator B (107) to perform drug tests for those under his or her jurisdiction, and a parole officer or therapist (or other entity) may use another test administrator (as indicated by the ellipses) to perform drug tests for the people they are working with. In such examples, the same person may be subject to drug tests from test administrator A, test administrator B, and other test administrators, potentially all within mere days of each other. Each of these employers, judges, or other entities may commit large amounts of money to be spent to have these drug tests performed. However, in at least in some of these cases, the drug test data could be shared among these entities for greater efficiency. For example, if a judge knew that an individual's therapist had already ordered a drug panel from test administrator B, and that the test was performed within the last few days, the judge may be able to avoid ordering a new drug panel, and might instead use the results from test administrator B (107).

However, each lab or medical test administering office may be set up to test for different drugs, different chemicals, different medications, different medical conditions, or other substances. Moreover, each testing center may refer to the substances or conditions they test for in different manners and may format their test data in different formats and in different ways. For instance, one lab may test for and note 200 different data points regarding an individual, while another lab may test for and note 2,000 different data points regarding the individual. These data points may include current test results and past test results, and may test for different substances and refer to those in different manners across the tests. Accordingly, among multiple different labs with different data points (e.g., drug panels or medical condition indicators) and different information points regarding each person under test, entities that need to see the results of these tests may see many different types of information from each of the different labs. Some types of information may be more relevant than other types. For instance, for any given individual, specific substances may be more at issue (e.g., past drug charges or past driving under the influence charges) and thus more relevant. Some substances or conditions may provide a better indication of the user's overall physical health and/or mental health. Accordingly, the embodiments herein may train machine learning models to identify and extract information that is most relevant to each user under test.

In some cases, these tests (and their corresponding results) may include other types of tests or lab work, in addition to (or at the exclusion of) drug tests. For example, the embodiments herein may access test data from a basic metabolic panel (BMP). The BMP may test for blood urea nitrogen, creatinine, glucose (i.e., blood sugar), carbon dioxide ($CO2$), calcium, or other items such as sodium, potassium, or chloride. In some cases, the embodiments herein may access test data from a comprehensive metabolic panel (CMP). The CMP may test for albumin, total protein, alkaline phosphatase (ALP), alanine amino transferase (ALT), aspartate amino transferase (AST), bilirubin, or other substances. Still further, the embodiments herein may access test data from a complete blood count (CBC) that may provide information about the numbers and kinds of cells in the blood, including red blood cells, white blood cells, and platelets.

Thus, as shown in FIG. 1, test administrator A (104) may test user 101 for substances X, Y, and Z (103) in test A (102). These substances may correspond to creatinine, glucose, and carbon dioxide, for example. On the other hand, test administrator B (107) may test user 101 for items E, F, G, and X (106) in test B (105). In this example, test administrator A may refer to the substances tested for as "substances," while test administrator B may refer to the substances tested for as items. These items may be named different things, but may still refer to the same substance. In some cases, a machine learning model may be trained to read names of substances, compare them to names of substances on other tests, and combine that knowledge with other information subsets to learn which substances are being tested for in each test (e.g., 102 or 105). In some cases, the machine learning model may be trained to look at amounts for each substance and may determine, based on the name or based solely on the amounts, which substance is most likely being tested for. Furthermore, in these determinations, the machine learning model may take into consideration the user under test, the user's substance history, and determine which substances are most likely to be tested for that user. Then, using some or all of this knowledge, the machine learning model may determine, for each test, which substances are being tested and which tested substances are most relevant to that specific user.

Other tests including urinalysis panels, lipid panel blood tests, hemoglobin blood tests, and other similar tests may each provide data that may be implemented by the systems herein. Indeed, any or all of these (or other) types of lab tests or lab work may produce information that may be stored in the optimized databases described herein. As such, references to a "drug test database" herein may be equally applied to medical tests or other lab work performed on people.

The embodiments described herein may be designed to optimize drug test database functionality by first receiving or otherwise accessing test data from multiple different drug test administration offices. These drug test administration offices may include substantially any type of lab or drug test processing center that tests individuals for specified substances including prescription medications and non-prescription drugs. The embodiments described herein may train machine learning models, which training process may implement artificial intelligence, deep learning, or other iterative approaches to analyze and compare reports and/or drug panels from each lab to each other lab.

The machine learning models may be trained to identify which disparate substances are being tested by each of the drug test administration offices, and to further identify other data points including subjective data points added by health care workers (e.g., doctors, nurses, pharmacists, etc.), police officers, judges, therapists, parole officers, or other individuals that have interacted with or have some type of supervisory role over the person under test (e.g., 101). The machine learning may access many different data points from many different labs to identify where similarities and crossover exist, and categorize those data points as being the same, similar, or different. The various categories of data may then be incorporated into a combined report that illustrates drug test results for the specified user under test from various drug test administration offices.

This combined report may then be presented to certain users or entities including those that have a supervisory role over the person under test. In some cases, the entities may authenticate a supervisory user or a monitoring user (e.g., a doctor, a pharmacist, a judge, etc.) and may provide the generated combined report to the authenticated monitoring user upon proper authentication. The combined report may indicate, potentially in columnar form, the test results for different chemicals and compounds from each of the disparate labs. The machine learning model may be trained to learn what each of the data points means in their various contexts (e.g., the unique context used by each lab), and may group potentially dissimilar information together based on a learned meaning of that data (e.g., after learning that seemingly dissimilar drug test data points are actually similar or refer to the same or a similar substance). The combined report may also show absent locations where a lab may not have tested for a specific drug or substance. Thus, each labs' results may be displayed in the report and, where no test data exists, those areas may be left blank. In this manner, the report may indicate to a reader which labs are testing for which substances and may provide other data points regarding users under test.

In some cases, the machine learning model may be trained to determine that at least some of the disparate medical test data (e.g., drug test data) between testing labs is to be altered or reformatted. For instance, if two types of disparate data are determined to be directed to similar categories of information, the systems described herein may be configured to alter data formats or alter underlying data structures representing that data. The altering may include reformatting the data, restructuring the data, recreating the data in another manner, or otherwise changing the data to align with medical test data or other data points provided by different test administrators (e.g., 104 or 107).

Still further, in at least some embodiments, users of a medical test database (e.g., 225 of FIG. 2) may be instructed to provide certain medical test data in a specified manner. For instance, the medical test database 225 may specify input formats for certain substance data, or may specify input requirements for different types of data points (indicating an amount of a substance, a timing in which the substance was taken, derivative substances in the user's body, observations made by doctors, therapists, judges, etc.). This may serve to standardize drug testing, for example, within an area, as each lab submitting drug test data may implement specified drug panels, specific formats, and/or specific methods of reporting drug test data to the database. This standardization may raise the standard of care for the users under test, as each person in a supervisory or monitoring role may have access to the same data, provided and presented in the same format. A pharmacy, for example, may see a combined report with three different lab test results from three different test administrators. Because the data is standardized across the three test administrators, the data may be formatted onto a single page and may show the most relevant test results for substances under test.

Figure 2:
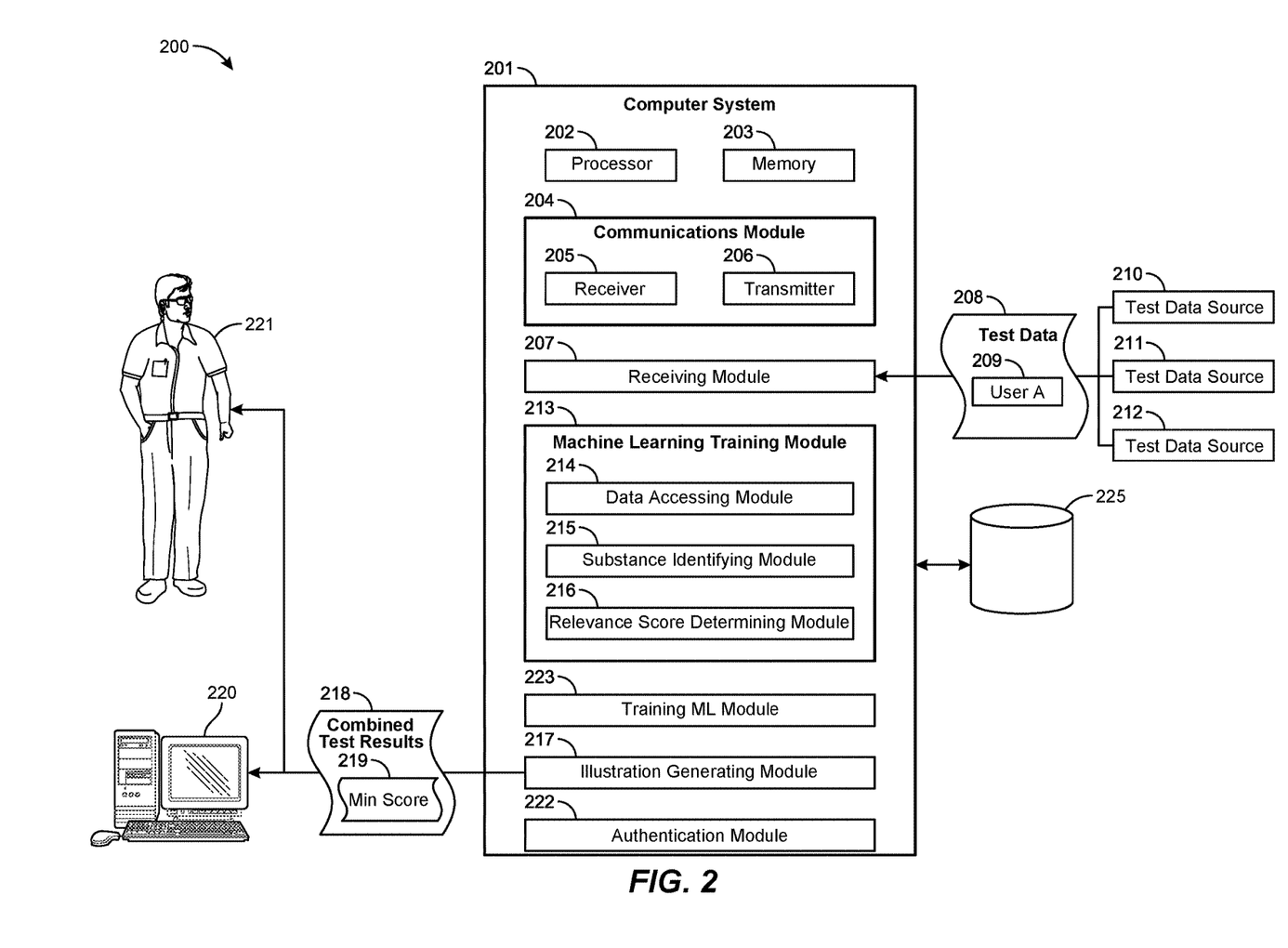
FIG. 2 illustrates an embodiment of a computing environment in which medical test database functionality is optimized.

Having a standardized database that can accept medical test results from a plurality of different labs may also allow test requisitioning entities to order fewer tests. Indeed, if a recent drug panel has been performed for a user, and the results of that panel are available in the comprehensive report, the entity may be able to avoid ordering a test for that user. This may save a great deal of money and duplicative effort. Such a database may also prevent users from visiting different doctors to get new prescription medications. Doctors may be able to look in the database 225 and see recent drug tests that have been performed for that user. If the user has not complied with their prescriptions, or is found to be self-medicating, the doctor may avoid writing a new prescription for that user. Thus, providing a medical test database that is available to many different entities that provides substance tests and other data points in an easy-to-read chart may allow those in supervisory roles to make better informed decisions regarding users under test. The medical test database may also, in this regard, increase the quality of medical test reports and may provide a means of direct comparison between different labs. As such, labs with the most optimal drug panels or other medical tests may be chosen to conduct the limited number of drug tests that need to be run.

FIG. 2 illustrates a computing environment 200 in which database functionality may be optimized and, specifically, the functionality of medical test databases. The computing environment 200 may include a computer system 201. The computer system 201 may include substantially any type of computing system including a desktop, laptop, tablet, server, smartphone, embedded system, or other type of computer system. The computer system 201 may include a physical processor 202 and memory 203, along with a communications module 204 that, itself, may include a receiver 205 and/or a transmitter 206 that are configured to transmit or receive data, either wirelessly or via a wired connection. In some cases, the communications module 204 may communicate with databases including test data sources 210, 211, and/or 212. Each of these test data sources may be databases that are configured to store test data (e.g., 208). In some cases, this test data 208 may be medical test data for a user under test (e.g., 101 of FIG. 1).

The receiving module 207 of computer system 201 may be configured to receive test data 208 for a specific user (e.g., user A (209)). In the example shown, the receiving module 207 may receive different test data 208 from each test data source 210-212. Thus, for instance, the user A may have been tested for various substances by an employer (with the test results being stored in test data source 210), by a judge (with the results being stored in test data source 211), and by a physician (with the results being stored in test data source 212). Other test data sources (e.g., governmental entities) may also be involved for any given user. The test data 208 may be transmitted from each of the test data sources 210-212 to the computer system 201. In some cases, the computer system 201 may include a data store or may be remotely connected to a data store 225 via a wired or wireless connection. In some cases, the test data 208 may be securely stored in the data store, while in other cases, the test data may only be temporarily stored in memory 203.

The computer system 201 may further include a machine learning training module 213. The machine learning training module 213 may be configured to train one or more machine learning models 223. The machine learning model 223 may be trained over time using different test data as inputs. The machine learning implementations and models described herein may implement substantially any type of machine learning to train a model (e.g., 223). At least in some cases, the machine learning training module 213 may be an inferential model.

As used herein, the term "inferential model" may refer to pure statistical models, pure machine learning models, or any combination of statistical and machine learning models. Such inferential models may include neural networks such as recurrent neural networks. In some embodiments, the recurrent neural network may be a long short-term memory (LSTM) neural network. Such recurrent neural networks are not limited to LSTM neural networks, and may have any other suitable architecture. For example, in some embodiments, the neural network may be a fully recurrent neural network, a gated recurrent neural network, a recursive neural network, a Hopfield neural network, an associative memory neural network, an Elman neural network, a Jordan neural network, an echo state neural network, a second order recurrent neural network, and/or any other suitable type of recurrent neural network.

In other embodiments, neural networks that are not recurrent neural networks may be used. For example, deep neural networks, convolutional neural networks, and/or feedforward neural networks, may be used. In some implementations, the inferential model may be an unsupervised machine learning model, for example, where previous data (on which the inferential model was previously trained) is not required. In other cases, the ML models may implement feedback loops to learn and improve themselves over time.

Thus, the machine learning training module 213 of computer system 201 may train a machine learning model 223 to perform various tasks. As part of this process, the machine learning training module 213 may implement different modules to perform the training. For instance, the machine learning training module 213 may implement a data accessing module 214 to access test data 208 from a variety of test data sources 210-212. The substance identifying module 215 may search through the accessed test data 208 (including past or present test data for user A or for other users) to identify different substances being tested. In some cases, test data sources may identify the substances in different manners including using different names or reference numbers. In some test data sources, substances may be clearly labeled, while in other cases, the substances may be abbreviated or may be referred to by different names, or may be referred to only with a number, or may be referred to using a non-standardized internal naming system. In such cases, the substance identifying module 215 may be configured to compare names, identifiers, numbers, or other indicators to determine which substances are being tested for.

In some cases, the substances being tested for may not be clear, even after an analysis of identifiers. In such examples, the embodiments herein may be configured to implement the substance identifying module 215 to identify substances based on detected amounts. For instance, many substances may have a common range for normal, healthy individuals, and may have another range for unhealthy individuals or individuals who are using drugs or alcohol. In such cases, and over time, the machine learning training module 213 may learn to recognize data values and determine which substances those values are linked to, even when the name or identifier is not clear. In other cases, the tested values may be used in combination with any identifier information that is available to determine which substances are being tested for. Once some or all of the substances have been identified, the relevance score determining module 216 of the machine learning training module 213 may be implemented to determine which of the test results is relevant for user A (209) or for another specified user.

For example, the relevance score determining module 216 of machine learning training module 213 may analyze the substances tested for and the users associated with the test results. The relevance score determining module 216 may learn, over time, to determine which substances are most relevant to a given user, and which substances are least relevant. Relevant substances may be those that an entity such as a judge, physician, parole officer, employer, etc. are testing for. The testing entity may be determined either directly from a test or may be inferred from which lab sent the test results. Over time, the relevance score determining module 216 may associate test ordering entities with certain substances (e.g., specific drugs or alcohol), and may determine that specific tested substances are more important to those test ordering entities than others. The relevance score determining module 216 may thereby determine that those substances are more relevant, and may provide those substances for presentation to a monitoring user 221 such as a physician, parole officer, etc., and/or to another specified entity 220.

For instance, the illustration generating module 217 of computer system 201 may generate a report or other illustration that may include those tested substances that were assigned at least a minimum relevance score 219. The report may include the combined test results 218 from each of the test data sources 210-212 and may be modified or filtered to show those test results most relevant to user A. In some cases, the monitoring user 221 may authenticate to the computer system using the authentication module 222 before they can view the combined test results 218.

Figure 3:
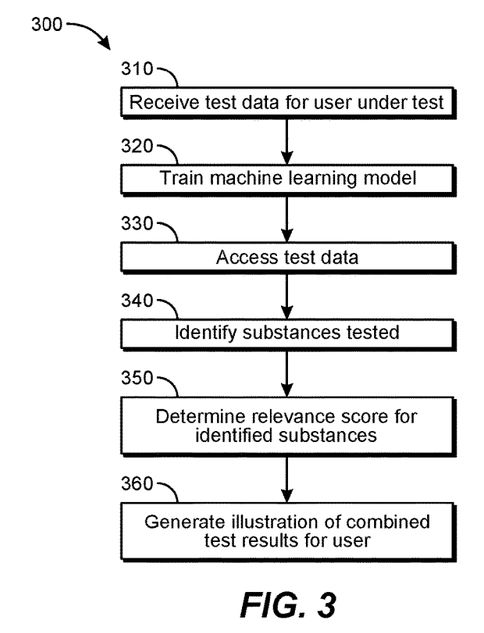
FIG. 3 illustrates an example method of optimizing medical test database functionality.

FIG. 3 illustrates a method 300 for optimizing a medical test database. At step 310, the method 300 includes receiving test data from multiple different test data sources for a specified user under test. The method 300 may further include training (at step 320) a machine learning model to: access (at step 330) the test data received from the test data sources for the same user under test, identify (at step 340) which disparate substances are being tested on the user by each of the different test data sources, and determine (at step 350) a relevance score for each of the identified substances being tested by the different test data sources. The method 300 may also include generating (at step 360) an illustration of combined test results for the user under test that includes those substances that meet at least a minimum relevance score.

In some cases, training the machine learning model (e.g., 223 of FIG. 2) to identify which disparate substances are being tested on the user (e.g., 209) by each of the different test data sources 210-212 may include determining that at least two of the different test data sources format the test data in different manner. Thus, for instance, test data sources 210 and 211 may each format or identify the same substance or group of substances in different manners. The substance identifying module 215 may determine that the test data sources 210 and 211 are using the different formats or identifiers, and may determine how each test data source refers to a given substance under test.

In cases where different test data sources use different formats, the computer system 201 may be configured to alter at least one of the data formats of the received test data 208 to align with another identified data format. In some embodiments, training the machine learning model to identify which disparate substances are being tested on the user by each of the different test data sources may include determining that at least two of the different test data sources identify substances under test using different identifiers. In such cases, the machine learning training module 213 may be configured to train the machine learning model 223 to compare similarities in substance identifiers in the different test data sources to determine if at least two substances that have different identifiers are testing for the same substance. If so, the machine learning model may make a note of such and indicate the similarity in the combined test results 218.

Moreover, in cases where different test data sources identify substances using different identifiers or fail to identify a given substance or group of substances, the machine learning training module 213 may train the machine learning model 223 to compare similarities in detected amounts of substance in the different test data sources to determine if at least two substances having different identifiers are testing for the same substance. For instance, the substance identifying module 215 may determine that test data sources 211 and 212 are providing test data 208 for user A (209) and may determine that similar amounts of certain substances are detected in the user's samples, but the substances may be referred to by different identifiers or no identifiers at all. In such cases, the substance identifying module 215 may look at past and/or present test data for user A (209) and/or other users, identify similar amounts for certain substances, and identify which substances are being tested for even if there are no identifiers or there are substances under different names. In some cases, the machine learning model 223 may be trained to compare both similarities in substance identifiers and similarities in detected amounts of substance in the different test data sources (e.g., 211 & 212) to determine if at least two substances having different identifiers are testing for the same substance.

In some embodiments, the authentication module 222 of computer system 201 may be implemented to authenticate a monitoring user 221 that is authorized to view the illustration of combined test results 218 and, upon authentication, present the generated illustration of combined test results to the authenticated monitoring user. The monitoring user 221 may view the combined test results 218 from substantially any type of computer system including a mobile or a stationary computer system. The monitoring user 221 may view the combined test results from multiple different labs or other test data sources, and may specifically view those test results that are most pertinent to a given user. The authentication may allow the monitoring user 221 to view those test results that are under their purview. Other test results for other users may be kept private.

Figure 4:
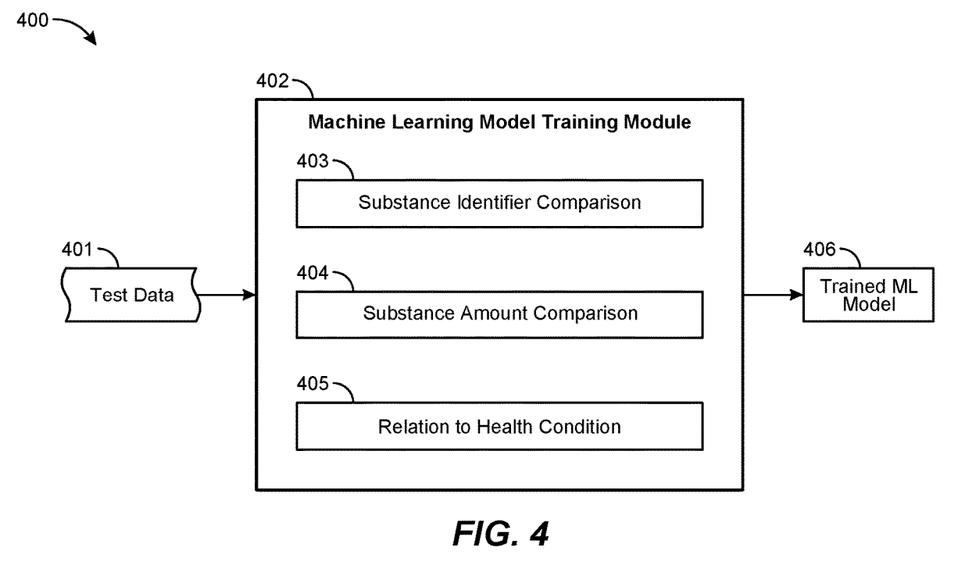
FIG. 4 illustrates a computing environment in which a machine learning model is trained to perform various tasks.

In some cases, as shown in FIG. 4, a computing environment 400 may include a machine learning model training module 402. This training module may be configured to train machine learning models to access test data 401, process the data, and output a trained machine learning model 406. In some embodiments, the training module 402 may train the machine learning model 406 to determine the relevance score for the identified substances using a substance identifier comparison 403 and/or a substance amount comparison 404. These comparisons may train the machine learning model 406 to more accurately and precisely identify substances under test for a given individual.

In some cases, identifying a substance under test may include determining whether the identified substances being tested are indicative of a specified health condition 405 of the user under test. Indeed, the presence of some substances in blood or urine may be indicative of a specific health condition 405. The machine learning model 406 may be trained based on past and/or present test data to associate certain substances or certain amounts of substances with health conditions 405. These health conditions may be noted in the combined test results 218 and may be presented to the monitoring user 221. In some cases, training the machine learning model to determine the relevance score for the identified substances may include determining a degree to which the identified substances being tested are indicative of a specified health condition of the user under test. Accordingly, in cases where an identified substance has a high correlation to a specific health condition 405, the computer system 201 may increase the relevance score to show that the results are highly relevant to the user.

As noted above, the test data sources may be medical test administration offices and the test data may include medical drug tests. The medical drug test may be a basic metabolic panel, a comprehensive metabolic panel, a complete blood count, or other type of medical drug test. In some cases, the medical test administration offices may implement a specific input format as a precondition for having their corresponding test data included in the generated illustration of combined test results. For instance, in a scenario where multiple different labs or medical test administration offices exist and those offices wish to use a common database service that is configured to generate and provide combined test results (e.g., 218) (e.g., database 225), the providers of the database may indicate to the medical test administration offices that specific input formats are to be used in order to have their test data included in the combined test results. The specified format may indicate, for instance, that certain substances are to be identified in a certain manner or that certain groups of substances are to include a common set of letters or numbers. In this manner, the database provider may at least partially standardize the test data received from the various test data sources.

In some embodiments, a system corresponding to the disclosed method may be provided. The system may include at least one physical processor and physical memory comprising computer-executable instructions that, when executed by the physical processor, cause the physical processor to: receive test data from different test data sources for a specified user under test, train a machine learning model to: access the test data received from the plurality of test data sources for the same user under test, identify which disparate substances are being tested on the user by each of the different test data sources, and determine a relevance score for each of the identified substances being tested by the different test data sources. The physical processor may further generate an illustration of combined test results for the user under test that includes those substances that meet at least a minimum relevance score.

In some embodiments, a non-transitory computer-readable medium corresponding to the method may be provided that includes one or more computer-executable instructions which, when executed by at least one processor of a computing device, cause the computing device to: receive test data from a plurality of different test data sources for a specified user under test, train a machine learning model to: access the test data received from the test data sources for the same user under test, identify which disparate substances are being tested on the user by each of the different test data sources, and determine a relevance score for each of the identified substances being tested by the different test data sources, and generate an illustration of combined test results for the user under test that includes those substances that meet at least a minimum relevance score.

Embodiments described herein may implement various types of computing systems. These computing systems are now increasingly taking a wide variety of forms. Computing systems may, for example, be handheld devices such as smartphones or feature phones, appliances, laptop computers, wearable devices, desktop computers, mainframes, distributed computing systems, or even devices that have not conventionally been considered a computing system. In this description and in the claims, the term "computing system" is defined broadly as including any device or system (or combination thereof) that includes at least one physical and tangible processor, and a physical and tangible memory capable of having thereon computer-executable instructions that may be executed by the processor. A computing system may be distributed over a network environment and may include multiple constituent computing systems.

Computing systems typically include at least one processing unit and memory. The memory may be physical system memory, which may be volatile, non-volatile, or some combination of the two. The term "memory" may also be used herein to refer to non-volatile mass storage such as physical storage media. If the computing system is distributed, the processing, memory and/or storage capability may be distributed as well.

As used herein, the term "executable module" or "executable component" can refer to software objects, routines, or methods that may be executed on the computing system. The different components, modules, engines, and services described herein may be implemented as objects or processes that execute on the computing system (e.g., as separate threads).

In the description that follows, embodiments are described with reference to acts that are performed by one or more computing systems. If such acts are implemented in software, one or more processors of the associated computing system that performs the act direct the operation of the computing system in response to having executed computer-executable instructions. For example, such computer-executable instructions may be embodied on one or more computer-readable media that form a computer program product. An example of such an operation involves the manipulation of data. The computer-executable instructions (and the manipulated data) may be stored in the memory of the computing system. Computing system may also contain communication channels that allow the computing system to communicate with other message processors over a wired or wireless network.

Embodiments described herein may comprise or utilize a special-purpose or general-purpose computer system that includes computer hardware, such as, for example, one or more processors and system memory, as discussed in greater detail below. The system memory may be included within the overall memory. The system memory may also be referred to as "main memory", and includes memory locations that are addressable by the at least one processing unit over a memory bus in which case the address location is asserted on the memory bus itself. System memory has been traditionally volatile, but the principles described herein also apply in circumstances in which the system memory is partially, or even fully, non-volatile.

Embodiments within the scope of the present disclosure also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the disclosure can comprise at least two distinctly different kinds of computer-readable media: computer storage media and transmission media.

Computer storage media are physical hardware storage media that store computer-executable instructions and/or data structures. Physical hardware storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the disclosure.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the principles described herein may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The present disclosure may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the present disclosure may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

In some cases, the embodiments herein may be configured to operate in such a cloud computing environment. Indeed, in at least some cases, the medical test database may be hosted, processed, and visualized in a cloud computing environment as described above. As such, the medical test database may be accessible using a desktop computer, a laptop, a tablet, a smartphone, or any other internet-enabled electronic device. In some cases, the embodiments herein may be provided in a software-as-a-service (SaaS) model, where the medical test database functionality is provided and operated as a software service provisioned by the cloud computing environment. The test data and associated software services may be made available to any internet-enabled devices and/or users that have access to the test data.

Still further, system architectures described herein can include a plurality of independent components that each contribute to the functionality of the system as a whole. This modularity allows for increased flexibility when approaching issues of platform scalability and, to this end, provides a variety of advantages. System complexity and growth can be managed more easily through the use of smaller-scale parts with limited functional scope. Platform fault tolerance is enhanced through the use of these loosely coupled modules. Individual components can be grown incrementally as business needs dictate. Modular development also translates to decreased time to market for new functionality. New functionality can be added or subtracted without impacting the core system.

In some cases, the computer system may include a communications module that communicates with other computing systems. The communications module may include any wired or wireless communication means that can receive and/or transmit data to or from other computing systems. The communications module may be configured to interact with databases, mobile computing devices (such as mobile phones or tablets), embedded or other types of computing systems.

Accordingly, methods, systems and computer program products are provided which allow users to remotely manage electrical devices. Moreover, electronic devices are provided which allow users to remotely manage electrical devices.

The concepts and features described herein may be embodied in other specific forms without departing from their spirit or descriptive characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

I claim:

1. At a computer system including at least one processor, a computer-implemented method for optimizing database functionality, the method comprising:
   receiving test data from a plurality of different test data sources for a specified user under test;
   training a machine learning model to:
      access the test data received from the plurality of different test data sources for the same user under test;
      identify which disparate substances are being tested on the user by each of the plurality of different test data sources; and
      determine a relevance score for each of the identified substances being tested by the plurality of different test data sources, wherein training the machine learning model to determine the relevance score for each of the identified substances includes determining a degree to which the identified substances being tested are indicative of a specified health condition of the user under test; and
   generating an illustration of combined test results for the user under test that includes those substances that meet at least a minimum relevance score.

2. The computer-implemented method of claim 1, wherein training the machine learning model to identify which disparate substances are being tested on the user by each of the plurality of different test data sources includes determining that at least two of the plurality of different test data sources format the test data in different manner.

3. The computer-implemented method of claim 2, further comprising altering at least a first data format of the received test data to align with a second determined data format.

4. The computer-implemented method of claim 1, wherein training the machine learning model to identify which disparate substances are being tested on the user by each of the plurality of different test data sources includes determining that at least two of the plurality of different test data sources identify substances under test using different identifiers.

5. The computer-implemented method of claim 4, further comprising training the machine learning model to compare similarities in substance identifiers in the different test data sources to determine if at least two substances having different identifiers are testing for the same substance.

6. The computer-implemented method of claim 4, further comprising training the machine learning model to compare similarities in detected amounts of substance in the different test data sources to determine if at least two substances having different identifiers are testing for the same substance.

7. The computer-implemented method of claim 4, further comprising training the machine learning model to compare both similarities in substance identifiers and similarities in detected amounts of substance in the different test data sources to determine if at least two substances having different identifiers are testing for the same substance.

8. The computer-implemented method of claim 1, further comprising:
   authenticating a monitoring user that is authorized to view the illustration of combined test results; and
   presenting the generated illustration of combined test results to the authenticated monitoring user.

9. The computer-implemented method of claim 1, wherein training the machine learning model to determine the relevance score for the identified substances includes determining whether the identified substances being tested are indicative of a specified health condition of the user under test.

10. A system comprising:
    at least one physical processor; and
    physical memory comprising computer-executable instructions that, when executed by the physical processor, cause the physical processor to:
       receive test data from a plurality of different test data sources for a specified user under test;
       train a machine learning model to:
          access the test data received from the plurality of different test data sources for the same user under test;
          identify which disparate substances are being tested on the user by each of the plurality of different test data sources; and
          determine a relevance score for each of the identified substances being tested by the plurality of different test data sources, wherein training the machine learning model to determine the relevance score for each of the identified substances includes determining a degree to which the identified substances being tested are indicative of a specified health condition of the user under test; and
       generate an illustration of combined test results for the user under test that includes those substances that meet at least a minimum relevance score.

11. The system of claim 10, wherein the test data sources include medical test administration offices.

12. The system of claim 11, wherein the medical test administration offices implement a specific input format as a precondition for having their corresponding test data included in the generated illustration of combined test results.

13. The system of claim 10, wherein the test data corresponds to a medical drug test.

14. The system of claim 13, wherein the medical drug test comprises at least one of a basic metabolic panel, a comprehensive metabolic panel, or a complete blood count.

15. The system of claim 10, wherein training the machine learning model to determine the relevance score for the identified substances includes determining whether the identified substances being tested are indicative of a specified health condition of the user under test.

16. The system of claim 10, wherein training the machine learning model to identify which disparate substances are being tested on the user by each of the plurality of different test data sources includes determining that at least two of the plurality of different test data sources identify substances under test using different identifiers.

17. The system of claim 16, wherein the physical processor further trains the machine learning model to compare both similarities in substance identifiers and similarities in detected amounts of substance in the different test data sources to determine if at least two substances having different identifiers are testing for the same substance.

18. A non-transitory computer-readable medium comprising one or more computer-executable instructions that, when executed by at least one processor of a computing device, cause the computing device to:
    receive test data from a plurality of different test data sources for a specified user under test;
    train a machine learning model to:

access the test data received from the plurality of different test data sources for the same user under test;
identify which disparate substances are being tested on the user by each of the plurality of different test data sources; and
determine a relevance score for each of the identified substances being tested by the plurality of different test data sources, wherein training the machine learning model to determine the relevance score for each of the identified substances includes determining a degree to which the identified substances being tested are indicative of a specified health condition of the user under test; and
generate an illustration of combined test results for the user under test that includes those substances that meet at least a minimum relevance score.

* * * * *